United States Patent [19]
Fujita et al.

[11] 4,205,127
[45] * May 27, 1980

[54] PROCESS FOR THE RENEWAL OF AN INSOLUBILIZED GLUCOSE ISOMERASE

[75] Inventors: Yoshimasa Fujita, Tokyo; Akiyoshi Matsumoto, Hino; Isao Miyachi; Nobuo Imai, both of Higashiyamato; Isao Kawakami, Machida; Tadashi Hishida, Tokyo; Akira Kamata, Yokohama, all of Japan

[73] Assignees: Mitsubishi Chemical Industries, Limited; Seikagaku Kogyo Company, Ltd., both of Tokyo, Japan

[*] Notice: The portion of the term of this patent subsequent to Sep. 12, 1995, has been disclaimed.

[21] Appl. No.: 917,256

[22] Filed: Jun. 20, 1978

Related U.S. Application Data

[63] Continuation of Ser. No. 780,843, Mar. 24, 1977, Pat. No. 4,113,568.

[51] Int. Cl.² .................. C12N 11/12; C12N 11/08; C12N 11/10
[52] U.S. Cl. .................. 435/179; 435/178; 435/180; 435/234; 435/815
[58] Field of Search .................. 195/68, 66 R, 31 F

[56] References Cited

U.S. PATENT DOCUMENTS

| 3,708,397 | 1/1973 | Sipos | 195/31 F |
| 4,002,576 | 1/1977 | Gregory et al. | 195/31 F X |
| 4,113,568 | 9/1978 | Fujita et al. | 195/68 |

OTHER PUBLICATIONS

Dorfner, Ion Exchangers Properties and Applications, pp. 21, 23 (1972), Ann Arbor Science Publishers, Inc.

Primary Examiner—Lionel M. Shapiro
Attorney, Agent, or Firm—Oblon, Fisher, Spivak, McClelland & Maier

[57] ABSTRACT

There is disclosed a process for the renewal of a deactivated insolubilized glucose isomerase which comprises subjecting an insolubilized glucose isomerase adsorbed onto an anion exchange resin, which has been used for isomerization of glucose into fructose to decrease its activity, to treatments by an aqueous mineral acid solution in combination with an aqueous alkaline solution, an aqueous electrolytic salt solution, an aqueous mineral acid or a mixture thereof to release adsorbed materials from the resin which is converted into a salt type and adsorbing fresh glucose isomerase to the regenerated resin to recover the activity of the insolubilized glucose isomerase.

15 Claims, No Drawings

PROCESS FOR THE RENEWAL OF AN INSOLUBILIZED GLUCOSE ISOMERASE

This is a continuation of application Ser. No. 780,843, filed Mar. 24, 1977, U.S. Pat. No. 4,113,568, issued Sept. 12, 1978.

This invention relates to a process for the renewal of an insolubilized glucose isomerase and, in more particular, to a process for the renewal of an insolubilized glucose isomerase adsorbed on and bonded to an anion exchange resin supporter which comprises desorbing the adsorbed materials from an insolubilized glucose isomerase which has been employed in the isomerization of glucose into fructose and adsorbing fresh glucose isomerase onto the supporter.

It has already been known that glucose is converted into fructose by glucose isomerase which is an enzyme capable of converting glucose into fructose and vice versa. Such glucose isomerase has been found in cells from a wide variety of microorganisms, for example, bacteria belonging to the genus Pseudomonas, Bacillus, Brevibacterium and Lactobacillus and Actinomycetes belonging to the genus Streptomyces as well as yeasts and, in particular for a practical purpose, an enzyme obtained from Streptomyces. Glucose isomerase is water soluble and, therefore, where the conversion of glucose into fructose is enzymatically conducted, it is convenient to subject such enzyme to an appropriate treatment to convert it into an insolubilized or immobilized form which can be used as a solid catalyst. Various supporters which adsorb glucose isomerase to form an insolubilized isomerase have already been proposed; for example, the Journal of Society of Japan Foodstuff Industry, 14, 12, p. 539–540 (1967) discloses the use of DEAE-Sephadex; U.S. Pat. No. 3,708,397 discloses DEAE-cellulose; and U.S. Pat. Nos. 3,788,945 and 3,960,663 and Japanese Patent Public Disclosures 80160/1974 and 53582/1975 disclose many types of ion exchange resins. Among such supporters, the anion exchange resin is preferred because it can adsorb a large amount of glucose isomerase per a given volume and the insolubilized isomerase produced possesses high activity and high stability. Isomerization of glucose with an insolubilized glucose isomerase is effected by either (1) mixing the insolubilized glucose isomerase with an aqueous glucose solution under agitation or (2) passing an aqueous glucose solution through a column packed with the insolubilized isomerase.

As the isomerization reaction continues, the activity of the insolubilized isomerase decreases gradually and the half-life period is in general from 15 to 60 days. The thus deactivated insolubilized isomerase is renewed by removing the insolubilized isomerase from the reaction system followed by desorbing the isomerase from the supporter and adsorbing fresh glucose isomerase thereon.

For the purpose of desorbing glucose isomerase from an ion exchange resin, Japanese Patent Publication 21514/73 suggests passing an aqueous inorganic salt solution, such as, sodium chloride or potassium chloride solution having a concentration of from 0.2 to 0.5 M, through a column packed with an insolubilized isomerase. That is, deactivated insolubilized glucose isomerase which has been used in the isomerization of glucose into fructose is subjected to a desorption treatment with an aqueous salt solution to desorb the isomerase from the ion exchange resin and readsorption treatment with fresh glucose isomerase, and the insolubilized isomerase thus renewed is used again for further isomerization, and such renewal cycles are repeatedly conducted. The inventors have found, however, an inherent disadvantage in this process. That is, as the renewal cycle is repeated, the amount of the isomerase desorbed from the anion exchange resin decreases and the ability of the resin for adsorbing the fresh isomerase is impaired with the result that the activity of insolubilized isomerase per unit volume lowers and, after repeating a few cycles, the anion exchange resin loses its capacity to adsorb the isomerase. It is believed that such defect is the result of accumulated contaminants, such as protein and metal salt adsorbed on the supporter.

It has been found that if deactivated insolubilized isomerase is treated with an aqueous mineral acid in combination with an aqueous alkaline solution, an aqueous electrolytic salt solution, an aqueous mineral acid or a mixture thereof, then glucose isomerase as well as undesirable protein and metal salt are effectively desorbed to regenerate the supporter resin while the regenerated resin entirely recovers its ability to adsorb the isomerase. Therefore, an insolubilized glucose isomerase derived from such regenerated resin and fresh isomerase possesses high enzymatic activity.

Accordingly, a primary object of this invention is to provide a process for the renewal of a deactivated insolubilized glucose isomerase which has been used in the isomerization reaction, which process comprises treating the deactivated insolubilized isomerase with an aqueous mineral acid solution in combination with an aqueous electrolytic salt solution and an aqueous alkaline material solution, an aqueous mineral acid or a mixture thereof to effect desorption of the isomerase and other materials from the anion exchange resin to form a regenerated resin in a salt form and adsorbing fresh glucose isomerase thereto.

This invention will be explained in detail hereunder.

The supporter onto which glucose isomerase is adsorbed include a wide variety of synthetic anion exchange resins. Among them, the preferred resin is a macroporous strong basic tertiary or quaternary ammonium type the matrix of which is a styrene-divinyl benzene copolymer, for example, Amberlite IRA 900, Amberlite IRA 93 and Amberlite IRA 904 which are available from Rohm & Hass Co., Philadelphia, Pa., U.S.A., and Diaion HPA 11 available from Mitsubishi Chemical Industries Ltd., Tokyo, Japan.

A conventional anion exchange resin prepared by copolymerizing a vinyl monomer such as styrene with a cross-linkable monomer such as divinyl benzene followed by introducing an anion exchange group, has a some micropores and, therefore, it is believed that its effective surface with which a polymeric material e.g. an enzyme can contact is only the outer surface of the resin and not the internal surface of the micropores. In contrast, the anion exchange resin employed according to this invention is a macroporous resin which has a large internal surface area.

Such macroporous anion exchange resin is conveniently prepared by any known process, for example, by copolymerizing a monovinyl monomer and a cross-linkable monomer in the presence of any material which is removable by a solvent and does not take part in the copolymerization, such as polystyrene. After completion of the polymerization, the resin obtained is treated with a solvent to extract the removable material, e.g. polystyrene, and anion exchange groups are introduced.

The anion exchange resin thus produced has, in general, macropores the radius of which ranges from $10^1$ to $10^3$ Angstroms. Such a macroporous anion exchange resin has been known in the art as in MR-type or macroporous type strong basic anion exchange resin, for example, reference is made to U.S. Pat. No. 3,960,663.

However, it should be noted that some macroporous anion exchange resins do not necessarily possess high adsorption ability for glucose isomerase. It has been found that the preferred anion exchange resin has a porosity of more than 4.5% measured according to the aqueous dextran solution method and an ion exchange capacity of more than 0.035 measured according to the polyanion salt decomposition method.

Although the mechanism in which glucose isomerase is adsorbed on a macroporous anion exchange resin and why the enzyme activity is developed have not yet been clarified in detail, it is believed that there is a synergistic effect of physical adsorption by the macropores in the resin and a certain chemical bonding force between the anion exchange group and the enzyme employed. This seems to be true, since very little glucose isomerase is adsorbed on a conventional gel type anion exchange resin which does not have any macropores and, on the other hand, a resin which has macropores but no ion exchange group can adsorb only a small amount of glucose isomerase and the activity of the resulting in solubilized glucose isomerase is also low. Thus, it is believed that the amount of glucose isomerase adsorbed on an anion exchange resin and the degree of the activity retention of the isomerase adsorbed depend upon the volume of internal pores which plays a role in the adsorption of the isomerase and the number of ion exchange groups in the pores.

The porosity measured by the aqueous dextran solution method corresponds to the total volume of macropores having a specific size through which pore dextran having a weight average molecular weight ($\overline{Mw}$) of 10,000 can pass but dextran having $\overline{Mw}$ of 2,000,000 cannot pass and such porosity has a close relationship to the amount of glucose isomerase which can be adsorbed on the anion exchange resin, therefore, it is believed that the adsorption of glucose isomerase will occur or will occur mainly in macropores of the specific size. It is further believed that the ion exchange capacity measured according to the polyanion salt decomposition method corresponds to the ion exchange capacity of the total surfaces area of such specific macropores.

Glucose isomerase is readily extracted from cells of a glucose isomerase producing microorganism such as Actinomycete belonging to the genus Streptomyces by ultrasonic treatment or treatment with egg white lysozyme. Adsorption of glucose isomerase onto an anion exchange resin to form an insolubilized isomerase is carried out by either (1) immersing the resin in an aqueous isomerase extract, optionally with agitation, for a predetermined period, then removing resin which has adsorbed the isomerase and washing it with water or (2) passing an aqueous glucose isomerase extract upwardly through a column packed with the resin to effect the adsorption while the resin being in a fluidized state.

A salt type anion exchange resin, such as phosphate, sulfate or chloride type is preferable to a free or hydroxyl type, since the former can adsorb more isomerase; accordingly the anion exchange resin onto which isomerase is to be adsorbed is subjected to pretreatment with an aqueous acid or salt solution to convert it into a salt type.

The larger the amount of isomerase adsorbed on the resin, the smaller is the degree of activity retention, and it has been found that the appropriate amount of glucose isomerase to be adsorbed on the resin is in general from 500 to 4000 U/ml-Resin, preferably 1000 to 2000 U/ml-Resin ("U" being the activity as will be defined hereinafter).

Isomerization of glucose into fructose with such insolubilized isomerase is conveniently carried out by a column process but a batch process with agitation may also be employed successfully.

In case of a column process, an aqueous glucose solution having a pH of from 6.5 to 8.5, a temperature of 55° to 70° C. and a concentration of 40 to 60% by weight is passed through a column packed with insolubilized isomerase at a liquid space velocity so as to maintain the degree of isomerization at from 35 to 50%. In order to maintain the activity of the isomerase for a long time, metal ions such as magnesium, cobalt and iron ions may be added alone or in combination to the aqueous glucose.

Where the isomerization reaction is continued under the abovementioned conditions for from about 30 to about 50 days, the activity of the insolubilized isomerase decreases to about half its starting level. It is recommended that the deactivated insolubilized isomerase is subjected to the renewal treatment according to this invention when the activity has decreased to 50 to 15% of the initial activity.

In the deactivated insolubilized isomerase, the supporter contains various adsorbed materials, mainly deactivated glucose isomerase as well as protein impurity and coloring material which are derived from the isomerase extract, inorganic materials such as magnesium salt, iron salt and cobalt salt which are added to the aqueous glucose and various kinds of saccharides.

According to this invention, an aqueous mineral acid solution facilitates desorption of all types of adsorbed materials from the supporter resin,—the glucose isomerase, inorganic materials, protein impurity, coloring material and saccharide abovementioned.

On the other hand, although the aqueous alkali solution does not have direct desorbing action, it swells the supporter resin, and the adsorbed materials are readily released from the swollen resin by subsequent acid treatment. Thus, if the aqueous alkali solution treatment is interposed between the acid treatments, the resin is swollen and shrunk repeatedly to facilitate desorption. An aqueous electrolytic salt solution or an aqueous mixture of electrolytic salt and alkali assists the desorption of the adsorbed coloring material.

In view of the above, according to this invention, deactivated insolubilized glucose isomerase is treated with an aqueous mineral acid solution in combination with an aqueous electrolytic salt solution, an aqueous alkali solution, an aqueous mineral acid or a mixture thereof to desorb the adsorbed materials from the supporter resin.

It should be noted that according to this invention it is not necessary to desorb all of the adsorbed materials. The purpose of the regeneration step is to restore the ability of the supporter resin to adsorb glucose isomerase with good activity retention. Complete desorption of all adsorbed materials from the supporter resin requires a large amount of regenerating agent so is uneconomical. It has been found that the satisfactory degree of desorption is such that the regenerated supporter resin can adsorb fresh glucose isomerase in an amount of from 500 to 4000 U/ml-Resin with a degree of activity retention of more than 70%, preferably more than 80%.

An aqueous mineral acid solution which may be used according to this invention is, for example, aqueous hydrochloric acid or sulfuric acid, and an aqueous alkali solution is, for example, an aqueous solution of an alkali metal hydroxide, such as sodium hydroxide or potassium hydroxide, both types of solutions being at a concentration of from 0.2 to 2 N, preferably 0.5 to 2 N.

Electrolytic salt solution is, for example, an aqueous solution of chloride or sulfate of an alkali metal, such as sodium chloride, potassium chloride, sodium sulfate or potassium sulfate, having a concentration of conveniently from 0.2 to 5 M.

In case of an aqueous mixture of electrolytic salt and alkali, the molar ratio thereof ranges from 20:1 to 1:2.

In carrying out the desorbing treatment according to this invention, aqueous regenerating agents are passed downwardly through a column packed with deactivated, insolubilized isomerase, followed by washing it, for example, by passing downwardly through the column desalted water 2 to 15 times the volume of the insolubilized isomerase.

The desorption treatment may be effected at room temperature; but, since the higher the temperature, the higher the desorbing efficiency, it is preferred to effect desorption at a temperature of from 50° to 75° C., taking into consideration the heat resistance of the supporter resin.

The anion exchange resin from which the isomerase has been desorbed is converted into a salt type by conveniently treating it with an aqueous mineral acid or an aqueous electrolytic salt solution thereby improving its ability to adsorb fresh glucose isomerase.

If the final step in the regeneration treatment is by an aqueous mineral acid or an aqueous electrolytic salt solution, the resulting regenerated resin is, of course, of a salt type.

The regeneration of the supporter resin according to this invention is, taking into consideration the desorbing efficiency of the absorbed materials, conveniently a treatment of the insolubilized glucose isomerase with a combination of an aqueous mineral acid solution with an aqueous alkali solution, an aqueous electrolytic salt solution, an aqueous mineral acid solution or a mixture thereof. More particularly, the regeneration is carried out by passage the following one or more aqueous solutions through the column packed with the deactivated insolubilized glucose isomerase;

(1) an aqueous mixture of a mineral acid and an electrolytic salt,
(2) an aqueous mineral acid and an aqueous alkali solution, or vice versa
(3) an aqueous mineral acid and an aqueous electrolytic salt solution, or vice versa
(4) an aqueous mineral acid and an aqueous mixture of an alkaline material and a electrolytic salt, or vice versa
(5) an aqueous mineral acid and an aqueous mixture of electrolytic salt and mineral acid,
(6) instead of the aqueous mineral acid in cases 2 to 4, an aqueous mixture of a mineral acid and an electrolytic salt is used,
(7) in addition to cases (1) to (4), an aqueous mineral acid is used in third step.

The supporter anion exchange resin in a salt type thus regenerated can adsorb fresh isomerase to form a renewed insolubilized glucose isomerase which is used for further isomerization.

According to the regeneration treatment of this invention, the enzymatic activity of the insolubilized glucose isomerase can be recovered repeatedly without any significant decrease of activity. The "aqueous dextran solution method", "polyanion salt decomposition method", "activity of glucose isomerase extracted", "degree of bonded glucose isomerase", "activity of insolubilized glucose isomerase" and "degree of activity retention of insolubilized glucose isomerase" referred to in the specification and claims are defined as follows.

1. AQUEOUS DEXTRAN SOLUTION METHOD

A jacketed column of 11 mm internal diameter is packed with 67 ml of a $SO_4$ type anion exchange resin having a void ratio of 33% in wet state to form a resin bed and any excess water is removed while the bed is maintained at a temperature of 50° C. A 1.5 wt.% aqueous solution of dextran having a weight average molecular weight ($\overline{M}w$) of 2,000,000 determined by the light scattering method is passed through the resin bed at a space velocity (SV) of 0.4 $hr^{-1}$ and the effluent is divided into 2 g fractions. The concentration of each effluent fraction is measured by a refractometer. The quotient obtained by dividing the volume of the effluent (Vf) by the volume of the resin bed (Vb) and the quotient obtained by dividing the dextran concentration of each effluent fraction (C) by the original dextran concentration of 1.5 wt.% (Co) are plotted on the horizontal axis and the vertical axis, respectively, to obtain a curve.

Similar procedures are repeated using a 1.5 wt.% aqueous solution of dextran having $\overline{M}w$ of 10,000 determined by the light scattering method to obtain a curve.

Then, the porosity is determined by dividing by the factor of 0.67 the difference between the values of Vf/Vb at the points where C/Co is 0.5 for each of the aqueous dextran solutions, the molecular weight being 10,000 and 2,000,000; respectively, usually the porosity is expressed as a percentage, so the value determined as above is multiplied by the factor of 100.

The porosity of the resin is measured by using a Kiriyama column available from Kiriyama Seisakusho, Japan, and "Dextran T 2,000" having $\overline{M}w$ of 2,000,000 and "Dextran T 10" having $\overline{M}w$ of 10,500 available from Pharmacia Fine Chemical Inc., New Jersey, U.S.A., said molecular weight being measured by the light scattering method using an immersion liquid refractometer type T available from Karl Zweiss A.G., West Germany.

In measuring the porosity of resin, it should be appreciated that a variation in the molecular weight of dextran by ±10% from the abovementioned ranges does not essentially affect the result; the narrower the distribution of the molecular weight, the better the result, but little or no substantial effect is observed by such variation in distribution.

2. POLYANION SALT DECOMPOSITION METHOD

A given amount of polystyrene having a number average molecular weight ($\overline{M}n$) of 10,000 measured by the vapor pressure method and a value of less than 1.06 obtained by dividing the weight average molecular weight measured by the light scattering method by the number average molecular weight is subjected to sulphonation with 98% sulfuric acid in an amount 10 times the weight of said polystyrene and silver sulfate, as catalyst, in an amount of 0.01 time at a temperature of 100° C. for 5 hours. The reaction product is brought to neutral by the addition of aqueous ammonia, and water is removed in vacuo to obtain a solid product, which is then extracted with methanol. From the extract, the methanol is removed in vacuo to obtain ammonium polystyrene sulfonate. One gram of the ammonium polystyrene sulfonate is dissolved in desalted water to make one liter of an aqueous solution. The solution is passed through a jacketed column of 8 mm internal diameter packed with 10 ml of an OH type anion exchange resin maintained at a temperature of 25° C. at a rate of 100 ml/hr for 5 hours. The effluent from the column in an amount of 500 ml is titrated with 1/10 N hydrochloric acid using a methyl orange indicator. The quotient obtained by dividing the amount of the hydrochloric acid required for titration (ml) by the factor of 100 is the ion exchange capacity (meq/ml-Resin).

The resin employed in measuring the ion exchange capacity is Mono-Disperse Polystyrene Standard ($\overline{Mw}$=10,000 and $\overline{Mw}/\overline{Mn}$<1.06) available from Pressure Chemical Co., Ltd. A variation in the average molecular weight by ±10% from the abovementioned range does not essentially affect the results.

3. ACTIVITY OF GLUCOSE ISOMERASE EXTRACTED

A mixture of 0.2 ml of a 1 M aqueous D-glucose solution, 0.2 ml of a 0.05 M aqueous $MgSO_4.7H_2O$ solution, 0.2 ml of a 0.5 M aqueous phosphate buffer solution (pH=7.2) and a given amount of aqueous glucose isomerase extract is diluted with water to make 2 ml. The resulting mixture is maintained at a temperature of 70° C. for 60 minutes to effect the glucose isomerization which is terminated by the addition of 2 ml of 0.5 M perchloric acid. The amount of fructose produced is determined by cystein carbazole method. The value obtained by dividing the amount of fructose produced by the amount of aqueous glucose isomerase extract is the activity, the unit of which is expressed by the abbreviation "U".

4. DEGREE OF BONDED GLUCOSE ISOMERASE

The total activity of glucose isomerase solution to be used for adsorption on anion exchange resin is measured and this value is designated as "A". After adsorption of glucose isomerase on an anion exchange resin, the resin is separated by filtration and washed with water, then the total activity of the combined filtrate and wash water is measured and this value is designated as "B".

The degree of bonded glucose isomerase (D.B.G.) is given by the following equation:

$$DBG = \frac{A-B}{A} \times 100 \, (\%)$$

5. ACTIVITY OF INSOLUBILIZED GLUCOSE ISOMERASE

To 1 of an aqueous solution containing glucose, $MgSO_4.7H_2O$ and phosphate buffer at a concentration of 0.1 M, 0.005 and 0.05 M, respectively, is added a given amount of insolubilized glucose isomerase and the mixture thus obtained is slowly stirred at a temperature of 70° C. for 60 minutes to effect the conversion. Then, the insolubilized isomerase is separated from the reacted solution and the amount of fructose so produced is determined according to the cystein carbazol method. The activity is calculated as in 3 above.

The unit "U" means the amount of glucose isomerase capable of producing one milligram of fructose under the conditions mentioned above.

6. DEGREE OF ACTIVITY RETENTION OF INSOLUBILIZED GLUCOSE ISOMERASE

The activity of insolubilized glucose isomerase measured according to 3 above is divided by the activity of aqueous glucose isomerase extract to be adsorbed on the resin; the quotient is multiplied by 100 the resulting value is the degree of activity retention expressed as a percentage.

This invention will be explained by means of Examples. However, it should be understood that this invention is in no way limited by these Examples.

In the Examples, "extraction of glucose isomerase", "adsorption of glucose isomerase to supporter" and "isomerization reaction" were carried out as follows.

EXTRACTION OF GLUCOSE ISOMERASE

Glucose isomerase "NAGASE", which is produced from the strain belonging to *Streptomyces phaeochromoges* and is available from Nagase Sangyo Kabushiki Kaisha, Osaka, Japan, was suspended in water and, after addition of a small amount of egg white lysozyme, the suspension was stirred to effect extraction. The extracted solution had an activity of glucose isomerase of 240 U/ml. (This was designated as "glucose isomerase extract A").

Following similar procedures, an extracted solution having an activity of 200 U/ml was produced from another lot of "NAGASE" ("glucose isomerase extract B").

ADSORPTION OF GLUCOSE ISOMERASE TO SUPPORTER

A sulphate type macroporous strong basic anion exchange resin "Diaion HPA 11", which is a styrene-divinyl benzene cross-linked copolymer having quaternary ammonium ion exchange group and is available from Mitsubishi Chemical Industries Ltd., Tokyo, Japan was suspended in an aqueous glucose isomerase extract in an amount 10 times the volume of the swollen resin and stirred at 50° C. for 6 hours to obtain an insolubilized glucose isomerase.

ISOMERIZATION REACTION

A. One hundred milliliters of the insolubilized glucose isomerase was packed to a jacketed column of 20 mm internal diameter through which an aqueous solution containing glucose, magnesium sulfate and iron sulfate at a concentration of 3 M, 5 mM and 0.1 mM, respectively, and having a pH of 7.5 was passed downwardly at a temperature of 60° C. and at such a space velocity that the average degree of isomerization was 45% for 30 days to convert glucose into fructose.

B. Procedures similar to those of the above process were repeated but the aqueous glucose solution was passed through at a temperature of 70° C. and at a space velocity of 5 hr$^{-1}$ for 16 days.

EXAMPLES 1 AND 2

According to the procedures of process A, glucose isomerization reaction was carried out with an insolubilized glucose isomerase which had been prepared by adsorbing glucose isomerase extract A on Dianion HPA 11 and had a degree of adsorption of glucose isomerase of 100% and an activity of 2400 U/ml-Resin. After completion of the isomerization, one liter of desalted water was passed downwardly through the column to wash the insolubilized isomerase and 600 ml of 1 N sulfuric acid and 2 l of desalted water were in turn passed downwardly through the column. From the supporter resin, 50% of adsorbed protein and 97% of adsorbed iron ion were desorbed.

The glucose isomerase extract A was adsorbed onto the supporter thus regenerated, the degree of adsorption of glucose isomerase being 100% and the activity being 2400 U/ml-Resin. Then, the glucose isomerization was carried out by process A.

After repeating 4 cycles of adsorption-isomerization-desorption, the degree of adsorption was observed to be 51% and the activity was 1224 U/ml-Resin, which values show inferior performance of the insolubilized isomerase. This insolubilized isomerase was used for carrying out the glucose isomerization.

Then, two portions of the insolubilized isomerase of 20 ml were packed in two columns through which the aqueous solutions in predetermined amount given in Table 1 were passed downwardly to regenerate the supporter resin.

Glucose isomerase extract A was adsorbed on each of the regenerated supporter resins and the activity and the degree of adsorption thereof were measured. The results are given in Table 1.

Table 1

| | Example 1 | | | Example 2 | |
|---|---|---|---|---|---|
| Regenerating agents | 1N $H_2SO_4$, | 120 ml | (1) | 1N $H_2SO_4$, | 120 ml |
| | $H_2O$, | 120 ml | (2) | $H_2O$, | 120 ml |
| | 1N NaOH, | 120 ml | (3) | Aqueous mixture of 0.1N NaOH and 0.5M $Na_2SO_4$, | 120 ml |
| | $H_2O$, | 120 ml | | | |
| | 1N $H_2SO_4$, | 120 ml | (4) | $H_2O$, | 120 ml |
| | $H_2O$, | 400 ml | (5) | 1N $H_2SO_4$, | 120 ml |
| | | | (6) | $H_2O$ | |
| Activity after readsorption (U/ml-Resin) | 1560 | | | 2208 | |
| Degree of bonded isomerase (%) | 65 | | | 92 | |
| Degree of activity retention (%) | 85 | | | 88 | |

Note:
$H_2O$ used was desalted water.

From Table 1, it is clear that according to the treatments of this invention, the ability of a supporter resin to adsorb glucose isomerase is recovered entirely.

EXAMPLES 3 TO 11

According to the procedures of process A, glucose was isomerized with an insolubilized isomerase prepared by adsorbing glucose isomerase extract B on a supporter resin of Diaion HPA 11 and having a degree of adsorption of 100% and an activity of 2000 U/ml-Resin. After completion of the isomerization, 1 N sulfuric acid, desalted water, 1 N sodium hydroxide, 1 N sulfuric acid and desalted water each in 500 ml were in turn passed downwardly through the column at room temperature. Glucose isomerase extract B was adsorbed to the regenerated supporter resin to form an insolubilized isomerase which was used for further isomerization. This cycle was repeated four times.

The fifth regeneration was conducted with 500 ml each of the solutions given in Table 2 to effect desorption of the adsorbed protein and iron ion. Glucose isomerase extract B was adsorbed to the regenerated supporter resin to form an insolubilized isomerase. The results are given in Table 2.

Table 2

| Example No. | 3 | 4 | 5 | 6 | 7* | 8* | 9* | 10* | 11* |
|---|---|---|---|---|---|---|---|---|---|
| Regenerating agent | (1) 1N $H_2SO_4$ | (1) 1N $H_2SO_4$ | (1) 1N NaOH | (1) 1N $H_2SO_4$ | (1) 0.5M $Na_2SO_4$ | (1) 1N NaOH | (1) Aqueous mixture of NaOH (1 mole/l) and $Na_2SO_4$ (0.5 mole/l) | (1) 1N NaOH | (1) 1N $H_2SO_4$ |
| | (2) $H_2O$ | (2) $H_2O$ | (2) $H_2O$ | (2) $H_2O$ | (2) $H_2O$ | (2) $H_2O$ | | (2) $H_2O$ | (2) $H_2O$ |
| | (3) 1N NaOH | (3) Aqueous mixture of NaOH (1 mole/l) and NaCl (1 mole/l) | (3) 1N $H_2SO_4$ | (3) Aqueous mixture of $H_2SO_4$ (0.5 mole/l) and NaCl (1 mole/l) | | | (2) $H_2O$ | (3) 0.5M $Mn_2SO_4$ | |
| | (4) $H_2O$ | (4) $H_2O$ | (4) $H_2O$ | (4) $H_2O$ | | | | (4) $H_2O$ | |
| | (5) 1N $H_2SO_4$ | (5) 1N $H_2SO_4$ | | (5) 1N $H_2SO_4$ | | | | | |
| | (6) $H_2O$ | (6) $H_2O$ | | (6) $H_2O$ | | | | | |
| Desorption of iron (%) | 98 | 99 | 95 | 99 | 1.1 | N.D. | N.D. | N.D. | 91 |
| Desorption of protein (mg/ml-Resin) | 6.5 | 9.2 | 5.2 | 4.1 | 1.65 | 0.91 | 3.2 | 2.7 | 3.5 |
| Degree of bonded (%) | 88.2 | 94.9 | 82.1 | 65.1 | 33.7 | 10 | 10 | 42.2 | 59 |
| Degree of activity retention | 85.6 | 87.2 | 85.9 | 81.0 | 72.9 | — | — | 73.3 | 86.6 |

Table 2-continued

| Example No. | 3 | 4 | 5 | 6 | 7* | 8* | 9* | 10* | 11* |
|---|---|---|---|---|---|---|---|---|---|
| (%) | | | | | | | | | |

Note:
*For comparative purpose
$H_2O$ used was desalted water

EXAMPLE 12

Glucose isomerase extract A was adsorbed to Diaion HPA 11 ($SO_4$ type) to form an insolubilized isomerase (the degree of adsorption being 100% and the activity being 2400 U/ml-Resin) which was used for glucose isomerization according to process B. After thoroughly washing with desalted water by passing through the column downwardly, two portions (each 20 ml) of the insolubilized isomerase were packed in two columns (columns A and B). In turn, 300 ml each of 1 M aqueous sodium chloride, 1 N sulfuric acid and desalted water was passed through downwardly at room temperature for column A and at 70° C. for column B. Then, glucose isomerase extract A was adsorbed to the regenerated supporter resins. The following Table 3 shows the results.

Table 3

| | Column A | Column B |
|---|---|---|
| Desorption of protein (%) | 54 | 85* |
| Desorption of iron (%) | 100 | 100 |
| Degree of bonded (%) | 91 | 100 |
| Activity retention (%) | 81 | 90 |

Note:
10% was desorbed in $H_2SO_4$ treatment.

What is claimed is:

1. A process for the renewal of an insolubilized glucose isomerase comprising the steps of:
    (1) desorbing the adsorbed materials from an insolubilized glucose isomerase by treating sequentially with an aqueous mineral acid in combination with an aqueous alkali solution, an aqueous electrolytic salt solution, an aqueous mineral acid or a mixture thereof, said insolubilized isomerase being glucose isomerase adsorbed on and bonded to a supporter of synthetic anion exchange resin and having been used in the isomerization of glucose into fructose,
    (2) converting said supporter resin into a salt type to regenerate the supporter, and
    (3) adsorbing fresh glucose isomerase on the regenerated supporter.
2. A process for the renewal of an insolubilized glucose isomerase according to claim 1, wherein said desorbing treatment is effected with an aqueous mineral acid and an aqueous alkali solution.
3. A process for the renewal of an insolubilized glucose isomerase according to claim 1, wherein said desorbing treatment is effected with an aqueous mineral acid and an aqueous mixture of an alkaline material and an electrolytic salt.
4. A process for the renewal of an insolubilized glucose isomerase according to claim 1, wherein said desorbing treatment is effected with an aqueous mineral acid and an aqueous electrolytic salt solution.
5. A process for the renewal of an insolubilized glucose isomerase according to claim 1, wherein said desorbing treatment is effected with an aqueous mixture of a mineral acid and an electrolytic salt.
6. A process for the renewal of an insolubilized glucose isomerase according to claim 1, wherein said desorbing treatment is effected at a temperature of from 50° to 70° C.
7. A process for the renewal of an insolubilized glucose isomerase according to claim 1, wherein said aqueous mineral acid is aqueous hydrochloric acid or sulfuric acid and said aqueous alkali solution is aqueous sodium hydroxide or potassium hydroxide.
8. A process for the renewal of an insolubilized glucose isomerase according to claim 1, wherein said aqueous mineral acid is aqueous hydrochloric acid or sulfuric acid and said aqueous mixture contains sodium hydroxide or potassium hydroxide and sodium chloride, potassium chloride, sodium sulfate or potassium sulfate.
9. A process for the renewal of an insolubilized glucose isomerase according to claim 1, wherein said aqueous mineral acid is aqueous hydrochloric acid or sulfuric acid and said aqueous electrolytic salt solution is aqueous sodium chloride, potassium chloride, sodium sulfate or potassium sulfate.
10. A process for the renewal of an insolubilized glucose isomerase according to claim 1, wherein each of said aqueous mineral acid and said aqueous alkali solution has a concentration of from 0.2 to 2 N.
11. A process for the renewal of an insolubilized glucose isomerase according to claim 1, wherein said aqueous mineral acid has a concentration of from 0.2 to 2 N and said aqueous mixture has a molar ratio of said electrolytic salt to said alkali of from 20:1 to 1:2.
12. A process for the renewal of an insolubilized glucose isomerase according to claim 1, wherein said aqueous mineral acid has a concentration of from 0.2 to 2 N and said aqueous electrolytic salt has a concentration of from 0.2 to 5 M.
13. A process for the renewal of an insolubilized glucose isomerase according to claim 1, wherein said desorbing treatment is subjected to an insolubilized glucose isomerase which has been deactivated to its initial activity of from 15 to 50%.
14. The process of claim 1, where subtreatment with an aqueous mineral acid occurs prior to said treatment with an aqueous alkali solution, an aqueous electrolytic salt solution and an aqueous mineral acid or a mixture thereof.
15. The process of claim 1, where subtreatment with an aqueous alkali solution and aqueous electrolytic salt solution or a mixture thereof, occurs prior to said treatment with an aqueous mineral acid.

* * * * *